United States Patent
Wang

(10) Patent No.: US 7,243,794 B2
(45) Date of Patent: Jul. 17, 2007

(54) TATTOO NEEDLE CASE WITH NEEDLE HEAD PROTECTION ARRANGEMENT

(76) Inventor: Ta Ching Wang, 4FL. 27, Lane 160, Hsin Sheng S. Rd., Sec. 1, Taipei (TW)

( * ) Notice: Subject to any disclaimer, the term of this patent is extended or adjusted under 35 U.S.C. 154(b) by 319 days.

(21) Appl. No.: 10/902,167

(22) Filed: Jul. 30, 2004

(65) Prior Publication Data
US 2006/0021890 A1 Feb. 2, 2006

(51) Int. Cl.
*B65D 85/24* (2006.01)
*A61B 17/34* (2006.01)

(52) U.S. Cl. ........................ 206/380; 206/469; 606/186

(58) Field of Classification Search ........ 206/380–383, 206/366, 443, 469; 30/368; 606/186
See application file for complete search history.

(56) References Cited

U.S. PATENT DOCUMENTS

| | | | | |
|---|---|---|---|---|
| 1,280,264 A | * | 10/1918 | Mapes | 206/381 |
| 3,074,540 A | * | 1/1963 | Beich et al. | 206/469 |
| 3,075,639 A | * | 1/1963 | Crawford | 206/469 |
| 3,951,263 A | * | 4/1976 | Vale | 206/382 |
| 4,210,239 A | * | 7/1980 | Takahashi | 206/382 |
| 4,243,141 A | * | 1/1981 | Takahashi | 206/380 |
| 4,266,667 A | * | 5/1981 | Ishigaki | 206/469 |
| 4,386,697 A | * | 6/1983 | Zocher | 206/383 |
| 5,067,611 A | * | 11/1991 | Hagmann et al. | 206/383 |
| 5,460,267 A | * | 10/1995 | Schiffer | 206/380 |
| 5,664,674 A | * | 9/1997 | Lynch, Jr. | 206/382 |
| 6,030,404 A | * | 2/2000 | Lawson et al. | 606/186 |
| 6,619,476 B2 | * | 9/2003 | Hoch et al. | 206/380 |
| 6,983,847 B2 | * | 1/2006 | Faller et al. | 206/757 |

* cited by examiner

*Primary Examiner*—Bryon P. Gehman

(57) ABSTRACT

A tattoo needle case including a seat having a front section, a rear section including a plurality of lengthwise, parallel grooves, and a breakable section at a joining line of the rear section and the front section, the breakable section includes a cavity; a plurality of needles, each needle having a rear portion disposed in one of the plurality of grooves and a front portion including a pointed end disposed in the cavity; and a sheath sleeved on the seat for fastening the needles in the rear section, whereby bending the front section will cause the front and rear sections to come apart at the breakable section and cause the front and rear portions of the needles to come apart at the breakable section respectively. The case can protect the stored needles, particularly the pointed ends thereof for preventing the needles from accidentally pricking users.

7 Claims, 6 Drawing Sheets

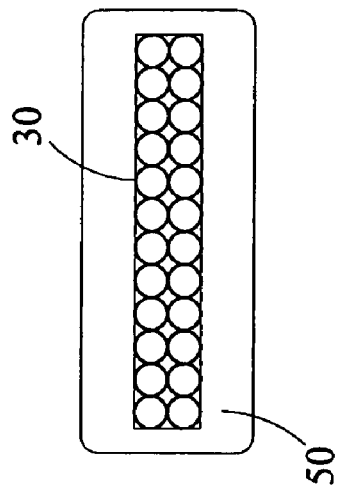
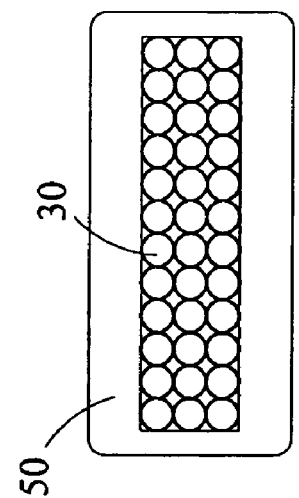
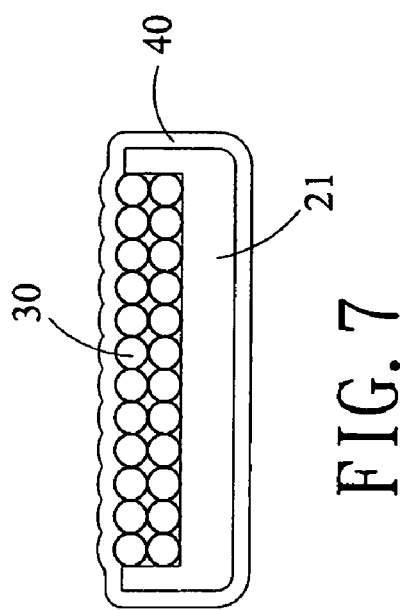
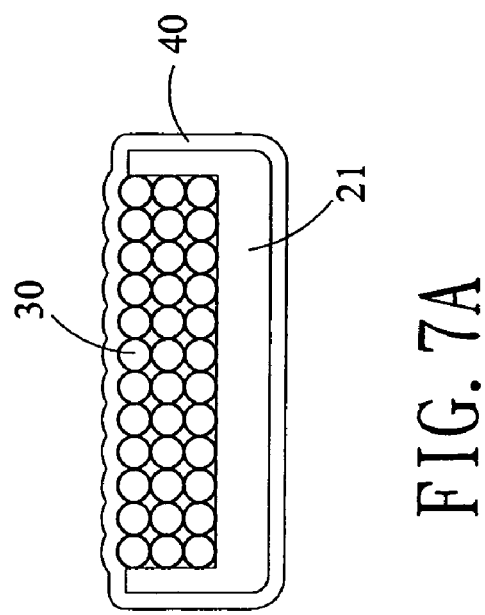

TATTOO NEEDLE CASE WITH NEEDLE HEAD PROTECTION ARRANGEMENT

BACKGROUND OF THE INVENTION

1. Field of the Invention

The present invention relates to tattoo needle cases and more particularly to an improved case for receiving a plurality of tattoo needles in which the needle heads are well protected for safety purpose and others.

2. Description of Related Art

Conventionally, a needle assembly is comprised of a plurality of needles arranged and fixed together on the major portion of the needle by utilizing a point solder technique or a stainless steel tube clamping technique. However, the pointed ends of needles may expose in either technique. Thus, a person may get pricked if sufficient care is not taken in operation. Moreover, accessing needles is not convenient. Further, its storage is disadvantageous. Hence, a need for improvement exists.

SUMMARY OF THE INVENTION

It is an object of the invention to provide a tattoo needle case with an arrangement for protecting pointed ends of a plurality of needles disposed in a parallel row therein. Moreover; the present invention can completely and satisfactorily solve the safety problem of being accidentally pricked by the needles during use. Further, the needle storage is easy and reliable.

It is another object of the present invention to provide a tattoo needle case having a needle fastening arrangement for retaining a plurality of needles in place.

It is a further object of the present invention to provide a tattoo needle case having a sufficient receiving space in cooperation with a needle fastening arrangement for retaining a plurality of needles in place.

To achieve the above and other objects, the present invention provides a tattoo needle case comprising a seat comprising a front section, a rear section including a receiving space having a plurality of lengthwise, parallel grooves, and a breakable section at a joining line of the rear section and the front section, the breakable section including a well in a middle and an opening at either side of the well, the front section including a cavity for receiving pointed ends of a plurality of needles; the plurality of needles are positioned in a parallel row, each needle having a rear portion disposed in the groove and a front portion including its pointed end disposed in the cavity; and a sheath sleeved on the seat for fastening the needles in the rear section, whereby bending and breaking the front section will cause the front and rear sections to come apart at the breakable section and cause the front portion with the pointed end of each needle to be exposed at the breakable section.

In one aspect of the invention, the cavity is trapezoidal and comprises an oblique side aligned with the breakable section.

In another aspect of the invention, the sheath is formed of thermoplastic material such that heating the thermoplastic sheath will tightly wrap both the seat and the needles together.

In further aspect of the invention, the sheath is formed of thin metal foil such that pressing the metal foil sheath will tightly wrap both the rear section and the needles together.

In still further aspect of the invention, the seat further comprises a cover including a plurality of lengthwise, parallel grooves on its underside, the grooves of the cover being engaged with the grooves of the rear section when the cover is put on the rear section for retaining the needles therebetween.

The above and other objects, features and advantages of the present invention will become apparent from the following detailed description taken with the accompanying drawings.

BRIEF DESCRIPTION OF THE DRAWINGS

FIGS. 7 and 7A are sectional views showing two configurations of rear section in which needle arrangements of two-layer and three-layer are illustrated respectively according to the invention; and FIGS. 8 and 8A are sectional views showing another two configurations of rear section in which needle arrangements of two-layer and three-layer are illustrated respectively according to the invention.

DETAILED DESCRIPTION OF THE PREFERRED EMBODIMENTS

Figure 1:
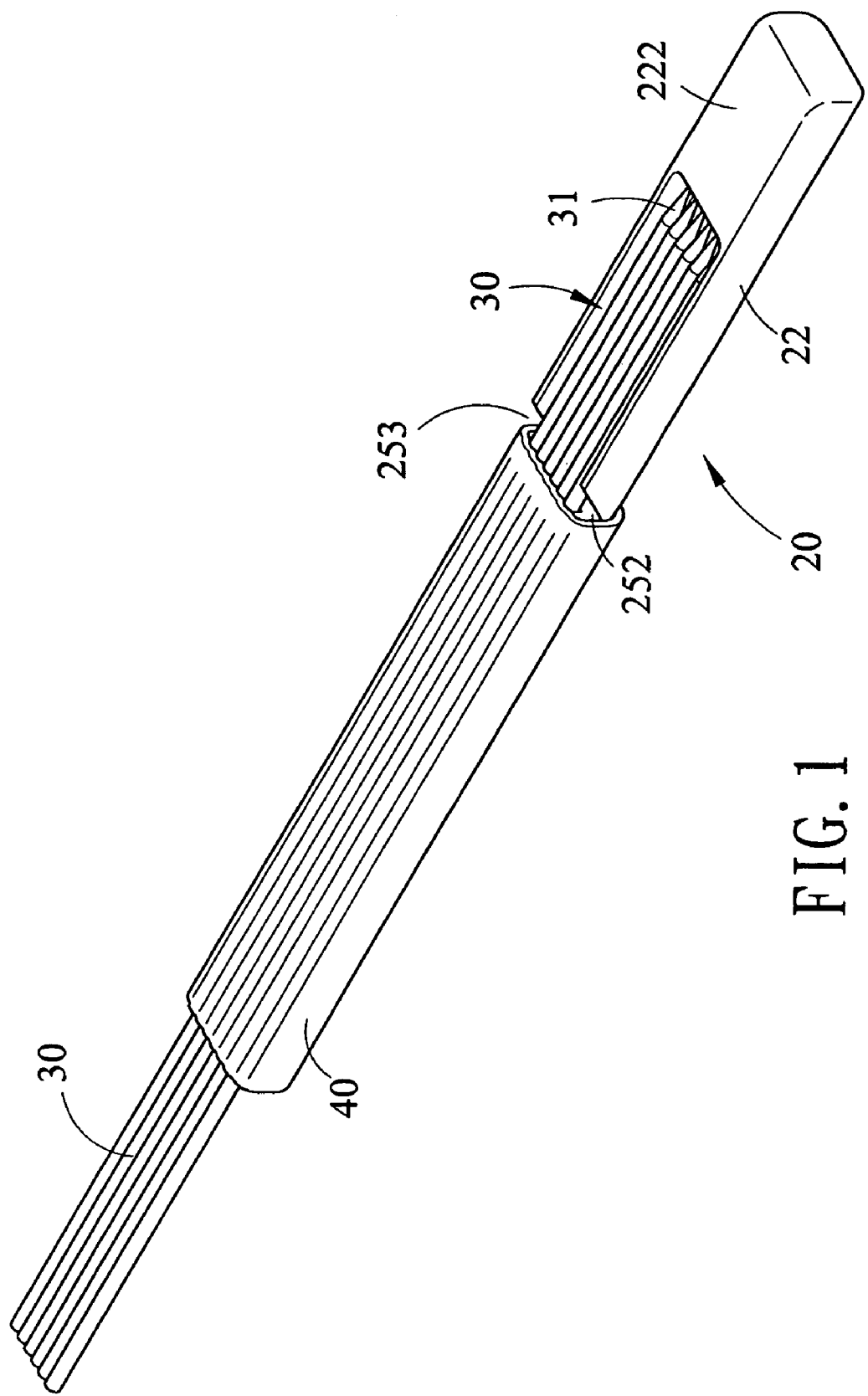
FIG. 1 is a perspective view of a first preferred embodiment of tattoo needle case according to the invention.
Figure 2:
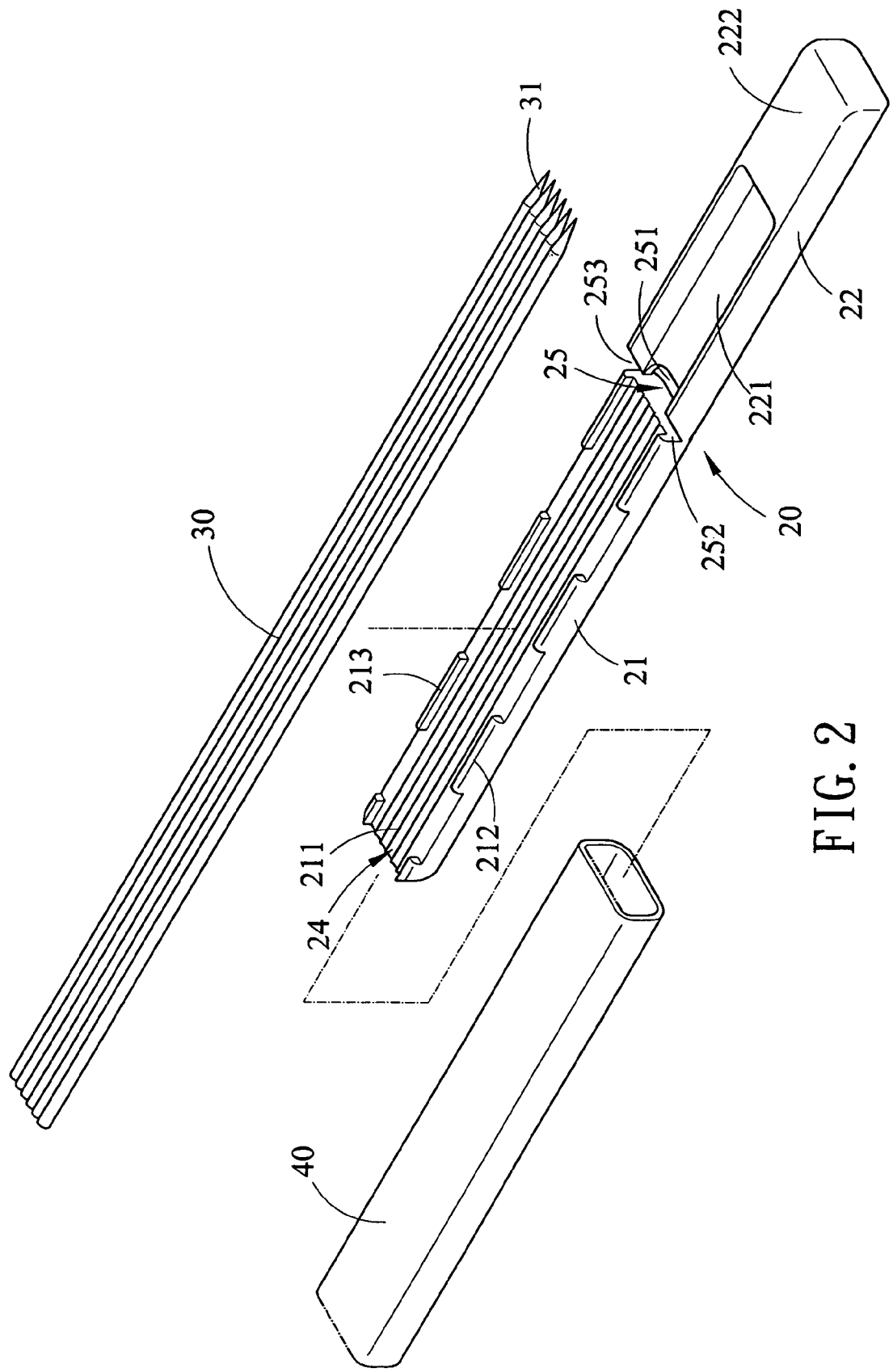
FIG. 2 is an exploded view of the case of FIG. 1.

Referring to FIGS. 1 and 2, there is shown a tattoo needle case constructed in accordance with a first preferred embodiment of the invention. The preferred embodiment is comprised of a seat 20, a plurality of needles 30, and a thermoplastic sheath 40. Each component will be described in detailed below.

The rectangular seat 20 comprises a rear section 21 and a front section 22 formed integrally therewith. The rear section 21 comprises a plurality of lengthwise, parallel grooves 211 with the needles 30 disposed therein, a plurality of first risers 212 formed on one side, a plurality of second risers 213 formed on the other side, a cavity 221 provided on the front section 22 with the pointed ends 31 of the needles 30 disposed therein, a forward flat 222, and a breakable section 25 at a joining line of the rear section 21 and the front section 22 and including a well 251 and two side openings 252 and 253.

The thermoplastic sheath 40 has a section of rectangle. The thermoplastic sheath 40 is sleeved on the seat 20 after placing the needles 30 on the grooves 211 of the rear section 21. The thermoplastic sheath 40 is adapted to tightly wrap both the seat 20 and the needles 30 after being subject to heat. As a result, the needles 30 disposed in the rear section 21 are protected by the thermoplastic sheath 40.

The pointed ends 31 of the needles 30 are completely concealed in the cavity 221 after wrapping the seat 20 by the thermoplastic sheath 40. Thus, the invention can completely and satisfactorily solve the safety problem of being accidentally pricked during use. Moreover, the needle storage is easy and reliable. In use, a user may hold the flat 222 to bend and break completely the front section 22 causing the rear and front section 21 and 22 to separate at the breakable section 25 (i.e., at the well 251 and the side openings 252 and 253). The breakable section 25 comprises a well 251 and two side openings 252 and 253. The well 251 facilitates the front section 22 to break and separate from the rear section 21. As a result, the parallel row of pointed ends 31 of the needles are exposed for being used. This process is quick, safe, and convenient.

Note that preferably, solder is applied around the seat 20 so that the fastening of the needles 30 can be successfully carried out by heating the solder and cooling thereafter.

Alternatively, tattoo needle case of the invention can be comprised of a seat 20 and a metal sheath 50 (see FIG. 8). The sheath 50 is sleeved on the rear section 21. Next, pressing the sheath 50 will tightly wrap both the rear section 21 and the needles 30. As a result, the needles 30 disposed in the rear section 21 are protected.

Figure 3:
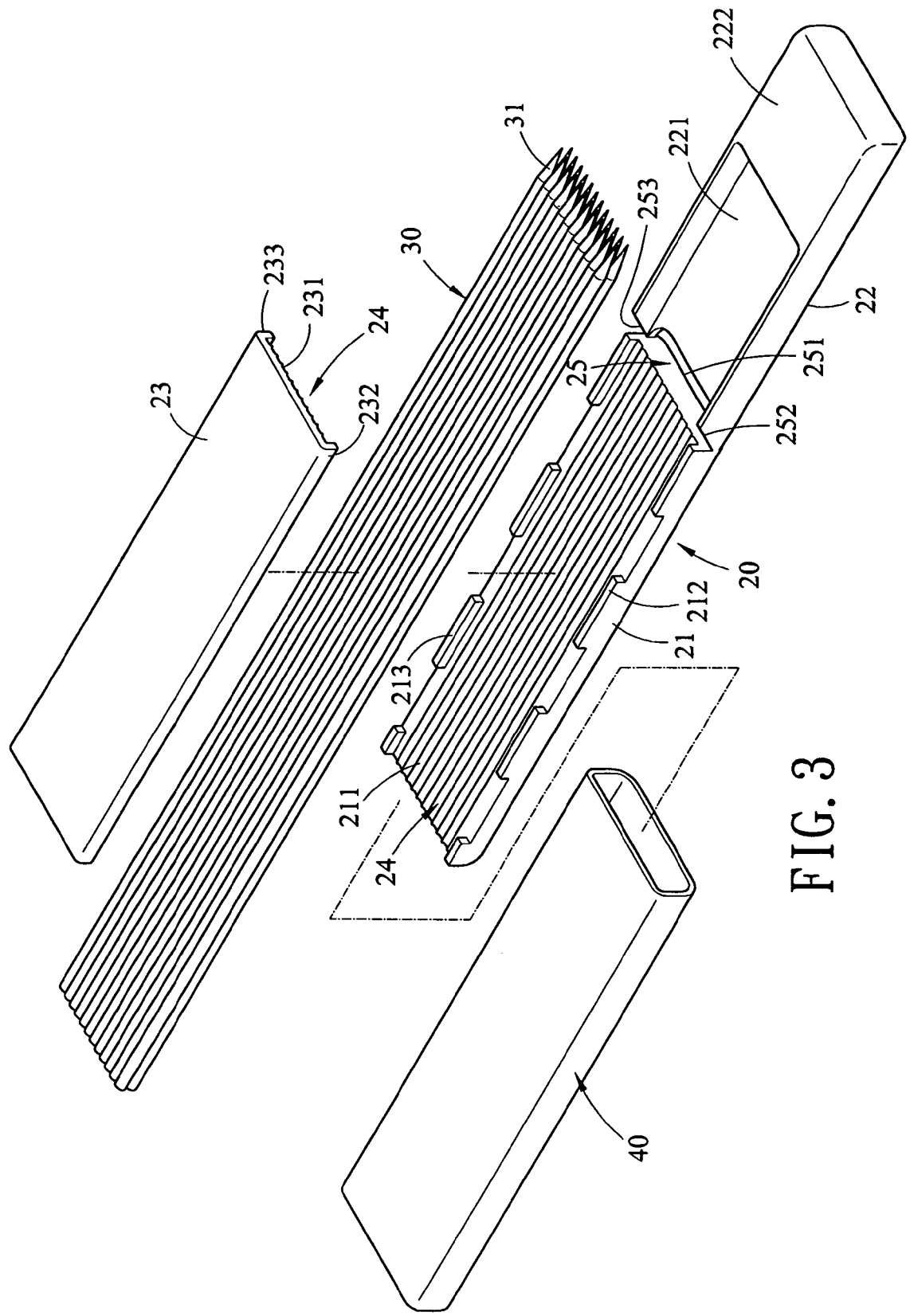
FIG. 3 is an exploded view of a second preferred embodiment of tattoo needle case according to the invention.

Referring to FIG. 3, there is shown a tattoo needle case constructed in accordance with a second preferred embodiment of the invention. The second preferred embodiment substantially has same structure as the first preferred embodiment. The characteristics of the second preferred embodiment are detailed below. The case comprises a seat 20, a plurality of needles 30, and a thermoplastic sheath 40.

The rectangular seat 20 comprises a rear section 21, a front section 22 formed integrally therewith, and a cover 23 put on the rear section 21 to form a receiving space 24 therebetween. The rectangular cover 23 comprises a plurality of lengthwise, parallel grooves 231 on its underside, a flange 232 formed on one side, and a second flange 233 formed on the other side. Similarly, the rear section 21 comprises a plurality of parallel grooves 211 with the needles 30 disposed therein, a plurality of first risers 212 formed on one side, a plurality of second risers 213 formed on the other side, a cavity 221 provided on the front section 22 with the pointed ends 31 of the needles 30 disposed therein, a forward flat 222, and a breakable section 25 at a joining line located between the rear section 21 and the front section 22 and including a well 251 and two side openings 252 and 253. The grooves 231 are adapted to engage with upper portions of the needles 30 when the cover 23 is put on the rear section 21. As such, the needles 30 are tightly retained by both the cover 23 (i.e., the grooves 231) and the rear section 21 (i.e., the grooves 211). Note that each of the receiving space 24 and the cavity 221 has a sufficient height so as to successfully store the needles 30 therein.

The thermoplastic sheath 40 has a section of rectangle. The thermoplastic sheath 40 is sleeved on the seat 20 after putting the cover 23 on the rear section 21 and placing the needles 30 in the grooves 211 in the receiving space 24 thereafter. The thermoplastic sheath 40 is adapted to tightly wrap both the seat 20 and the needles 30 after being subject to heat. As a result, the needles 30 disposed in the rear section 21 are protected by the thermoplastic sheath 40. Moreover, preferably, liquid adhesive is applied after placing the needles 30 in the rear section 21 and sleeving the thermoplastic sheath 40 thereon. As such, the fastening of the needles 30 can be successfully carried out by heating the adhesive and cooling thereafter. Still preferably, solder is applied so that the fastening of the needles 30 can be further enhanced by heating the solder and cooling thereafter.

Likewise, the pointed ends 31 of the needles 30 are disposed in the cavity 221 after wrapping the seat 20 by the thermoplastic sheath 40. Thus, the invention can completely and satisfactorily solve the safety problem of being accidentally pricked during use. Moreover, the needle storage is easy and reliable. In use, a user may hold the flat 222 to bend the front section 22 in order to cause the rear and front section 21 and 22 to come apart at the breakable section 25 (i.e., at the well 251 and the side openings 252 and 253). The breakable section 25 has a well 251 and two side openings 252 and 253. The Provision of the well 251 will facilitate the front section 22 to break and separate from the rear section 21 when used. As a result, the two parallel rows of pointed ends 31 of the needles are exposed for being used. This process is quick, safe, and convenient.

Figure 4:
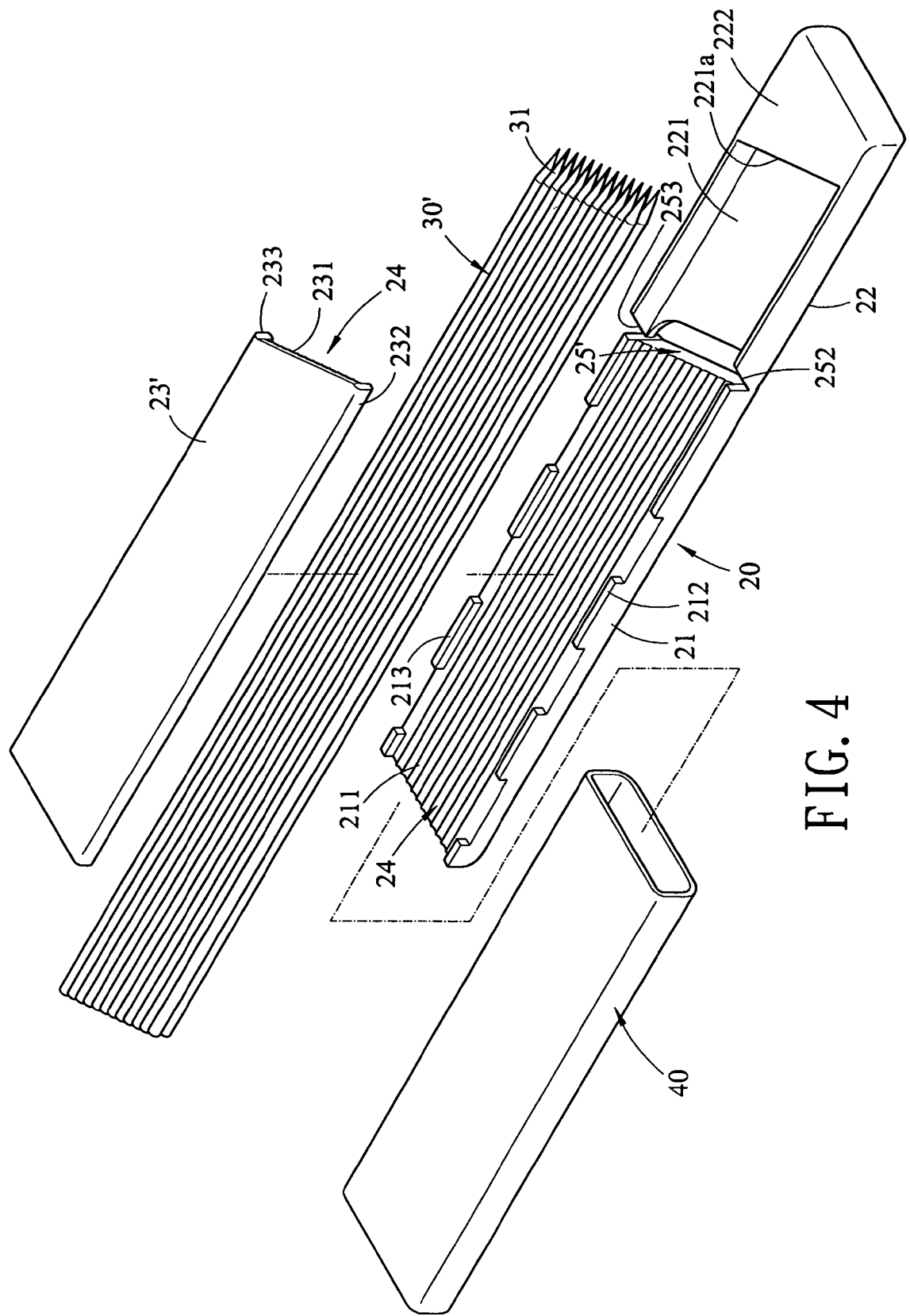
FIG. 4 is an exploded view of a third preferred embodiment of tattoo needle case according to the invention.

Referring to FIG. 4, there is shown a tattoo needle case constructed in accordance with a third preferred embodiment of the invention. The third preferred embodiment substantially has same structure as the second preferred embodiment. The characteristics of the third preferred embodiment are detailed below. The cavity 221 is a trapezoid and comprises an oblique side 221a aligned with the breakable section 25. Each of the front end of the cover 23' and the breakable section 25' is oblique and is substantially parallel to the side 221a. The lengths of the needles 30' exposed from the cover 23' and the breakable section 25' are about the same after breaking the front section 22. In other words, the prolonged portions of the obliquely disposed needles 30' can be supported by the breakable section 25' and the front end of the cover 23' by the provisions of the breakable section 25' and the cover 23'. As a result, strength of the seat 20 can be enhanced for accommodating elongated needles. Note that each of the front end of the cover 23' and the breakable section 25' can be formed as a curve or arc depending on applications. Also, the pointed ends 31 of the needles 30' are in close proximity with the curve or arc.

Figure 5:
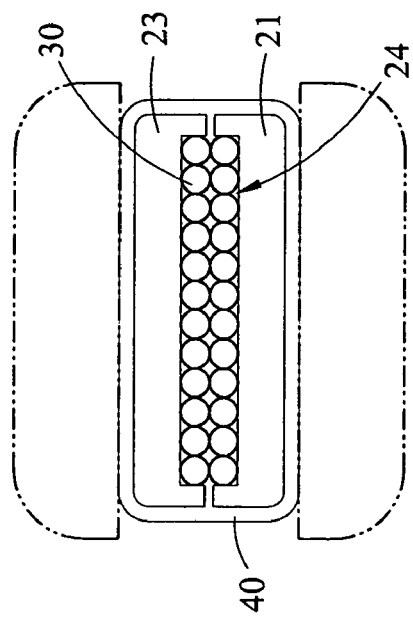
FIGS. 5 and 5A are sectional views showing needle arrangements of two-layer and three-layer respectively according to the invention.
Figure 5A:
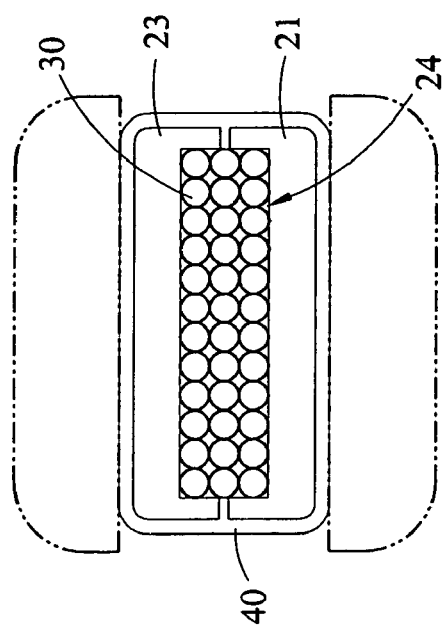

Referring to FIGS. 5 and 5A, needles 30 are arranged in two layers and three layers in the receiving space 24 formed by the rear section 21 and the cover 23 respectively. The two-layer or three-layer arrangement can provide a convenient and quick use of the needles.

Figure 6:
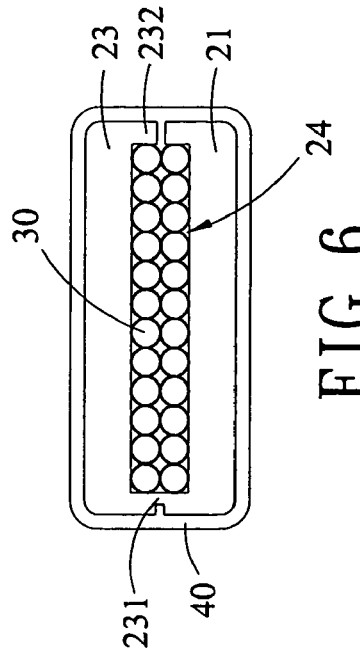
FIGS. 6 and 6A are sectional views showing two configurations of cover in which needle arrangements of two-layer and three-layer are illustrated respectively according to the invention.
Figure 6A:
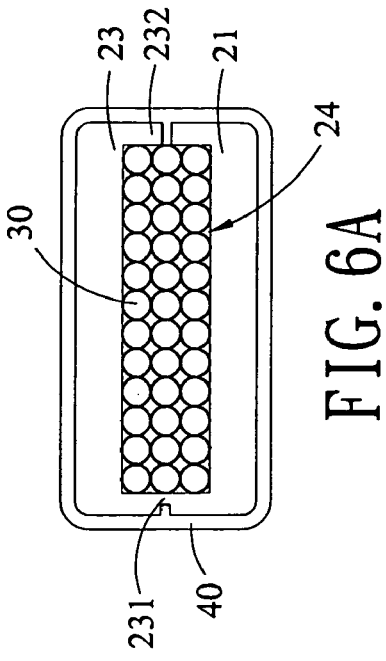

Referring to FIGS. 6 and 6A, the grooves 231 of the cover 23 are engaged with the corresponding grooves 211 of rear section 21. Also, the cover 23 are spaced apart from the rear section 21 by the side flanges 232. In a mounting operation, first place the needles 30 in the receiving space 24 and next put the cover 23 thereon for concealing the needles 30. Next, put the thermoplastic sheath 40 thereon and heat the same for fastening.

Referring to FIGS. 7 and 7A, needles 30 are arranged in two layers and three layers in the rear section 21 respectively. Next, put the thermoplastic sheath 40 thereon and heat the same for fastening both the rear section 21 and the needles.

Referring to FIGS. 8 and 8A, needles 30 are arranged in two layers and three layers in the rear section 21 respectively. Next, put the metal sheath 50 thereon. Next, pressing the sheath 50 will tightly wrap both the rear section 21 and the needles 30. As a result, the needles 30 disposed in the rear section 21 are protected.

While the invention herein disclosed has been described by means of specific embodiments, numerous modifications and variations could be made thereto by those skilled in the art without departing from the scope and spirit of the invention set forth in the claims.

What is claimed is:

1. A tattoo needle case comprising:
   a) a seat having:
      i) a front section movable between first and second positions and having a cavity;
      ii) a rear section having a receiving space having a predetermined height; and iii) a breakable section located between the front section and the rear section;
b) a plurality of needles located in the receiving space and having pointed ends, the plurality of needles being arranged in at least one parallel row; and
c) a sheath being spaced apart from the front section and encasing the rear section of the seat and securing the plurality of needles in the rear section,
wherein, when the front section is located in the first position, the front section is connected to the rear section by the breakable section and the pointed ends of the plurality of needles are located in the cavity of the front section,
wherein, when the front section is located in the second position, the breakable section is broken and the front section is separated from the rear section, and the pointed ends of the plurality of needles extend outwardly from the rear section of the seat.

2. The tattoo needle case according to claim 1, wherein the rear section has a plurality of rear section grooves extending along a top thereof, one of the plurality of needles is inserted into each of the plurality of rear section grooves.

3. The tattoo needle case according to claim 2, wherein the seat has a cover covering the rear section and having a plurality of cover grooves located on a bottom thereof, the plurality of cover grooves extend parallel along a length of the cover, one of the plurality of cover grooves aligning with each of the plurality of rear section grooves.

4. The tattoo needle case according to claim 1, wherein the breakable section has a well and two side openings, one of the two side openings is located on each of two opposing sides of the well.

5. The tattoo needle case according to claim 1, wherein the cavity is a trapezoid having an oblique side located adjacent to the breakable section, the pointed ends of the plurality of needles protrude outwardly from the oblique side.

6. The tattoo needle case according to claim 1, wherein the sheath is made of thermoplastic material surrounding both the seat and the plurality of needles.

7. The tattoo needle case according to claim 1, wherein the sheath is made of metal, the sheath surrounding both the seat and the plurality of needles.

* * * * *